(12) United States Patent
Hauth et al.

(10) Patent No.: US 10,258,430 B2
(45) Date of Patent: Apr. 16, 2019

(54) METHOD FOR THE VIRTUAL PROCESSING OF A DENTAL MODEL

(71) Applicant: DENTSPLY SIRONA Inc., York, PA (US)

(72) Inventors: Steffen Hauth, Mainz (DE); Sascha Schneider, Mühltal (DE)

(73) Assignee: DENTSPLY SIRONA Inc., York, PA (US)

( * ) Notice: Subject to any disclaimer, the term of this patent is extended or adjusted under 35 U.S.C. 154(b) by 875 days.

(21) Appl. No.: 14/770,550

(22) PCT Filed: Mar. 3, 2014

(86) PCT No.: PCT/EP2014/054056
§ 371 (c)(1),
(2) Date: Aug. 26, 2015

(87) PCT Pub. No.: WO2014/131909
PCT Pub. Date: Sep. 4, 2014

(65) Prior Publication Data
US 2016/0008109 A1    Jan. 14, 2016

(30) Foreign Application Priority Data

Mar. 1, 2013  (DE) .................. 10 2013 203 585

(51) Int. Cl.
*G06F 17/50* (2006.01)
*A61C 5/77* (2017.01)
(Continued)

(52) U.S. Cl.
CPC ............ *A61C 5/77* (2017.02); *A61C 13/0004* (2013.01); *A61C 13/0022* (2013.01); *A61C 13/34* (2013.01)

(58) Field of Classification Search
CPC ........................................................ A61C 5/77
(Continued)

(56) References Cited

U.S. PATENT DOCUMENTS

| 7,801,632 B2 | 9/2010 | Orth et al. |
| 8,483,857 B2 | 7/2013 | Orth |

(Continued)

FOREIGN PATENT DOCUMENTS

| DE | 102004038136 A1 | 2/2006 |
| DE | 102006021640 B3 | 10/2007 |

(Continued)

OTHER PUBLICATIONS

Jun. 13, 2014 International Search Report, in PCT Application No. PCT/EP2014/054056, 16 pp.
(Continued)

*Primary Examiner* — Hugh M Jones
(74) *Attorney, Agent, or Firm* — Dentsply Sirona Inc.

(57) ABSTRACT

The invention relates to a method for the virtual post-processing of a first virtual three-dimensional dental model (14) of a dental prosthesis (28), said model having been created during the planning of the prosthesis (28). The first virtual dental model (14) is processed virtually after the planning stage in an additional method step (18, 31) by adapting at least one three-dimensional aesthetic surface structure (17) already in existence to the first dental model (14) by means of a virtual tool (10) with the aid of a computer (4) and a display device (6) and by subsequently inserting said structure into the first dental model (14). The aesthetic surface structure (17) has a predetermined form, size and/or a predetermined impression depth (41), and a tooth surface (19) of the dental model (14) is at least partially replaced by the adapted aesthetic surface structure (15, 17).

13 Claims, 2 Drawing Sheets

(51) Int. Cl.
*A61C 13/00* (2006.01)
*A61C 13/34* (2006.01)

(58) Field of Classification Search
USPC .............................................. 703/1
See application file for complete search history.

(56) References Cited

U.S. PATENT DOCUMENTS

| | | |
|---|---|---|
| 2006/0008776 A1 | 1/2006 | Orth et al. |
| 2006/0070176 A1 | 4/2006 | Kondo |
| 2009/0181346 A1 | 7/2009 | Orth |
| 2013/0325415 A1 | 12/2013 | Willers |

FOREIGN PATENT DOCUMENTS

| | | |
|---|---|---|
| DE | 102010063124 A1 | 6/2012 |
| EP | 1 614 397 A1 | 1/2006 |
| JP | 2006-102243 A | 4/2006 |
| JP | 2009-536056 A | 10/2009 |
| WO | 2012/080380 A1 | 6/2012 |

OTHER PUBLICATIONS

Sep. 20, 2013 German Official Action in German Patent Appln. 10 2013 203585.3, 12 pp.
Ralf Suckert, "Funktionelle Frontzahnästhetik," Verlag Neuer Merkur GmbH, 1990, pp. 102-109, 111, 112, 114.
Office Action in Japanese Patent Application No. 2015-559520, dated Apr. 16, 2018 (with English translation), 12 pp.

METHOD FOR THE VIRTUAL PROCESSING OF A DENTAL MODEL

TECHNICAL FIELD

The invention relates to a method for the virtual post-processing of a first virtual three-dimensional dental model of a dental prosthesis, said model having been created during the planning of the prosthesis.

PRIOR ART

Several methods are known in the prior art for processing a three-dimensional dental model by means of a virtual tool. The dental model is planned automatically in a first step by means of a computer taking into account the neighboring teeth, the opposing antagonists, and other factors. Then the planned dental model of the dental prosthetic part is ground from a blank with a CAD/CAM machine tool. Then the dentist or dental technician etches or grinds fine surface structures in the visible aesthetic surfaces of the dental prosthesis in a post-processing step using a processing instrument.

On pages 102 to 108, the reference book, "Funktionelle Frontzahn-Ästhetik" by Ralf Suckert (1990) describes the manual insertion of aesthetic surface structures in a produced dental prosthesis using different grinding instruments for surface processing.

A disadvantage of this method is that the aesthetic surface structures are inserted manually by a dentist or dental technician in an elaborate manner. This manual post-processing step requires a great deal of experience and skill in the imitation of natural surface structures in order to achieve an aesthetic impression of a natural tooth.

DE 102004038136 A1 discloses a method for the construction of an aesthetic surface of a dental prosthesis, wherein three-dimensional data of this tooth surface of a saved tooth are used at least as part of the surface of the dental prosthesis to be produced, wherein the extent of the tooth surface is determined and arranged in the region of a preparation site. The size of the tooth surface can also be changed so that adaptation to the neighboring teeth is enabled.

A disadvantage of this method is that the size of an existing tooth surface from a database is adapted to the dental prosthesis to be produced. Individual adaptation of the tooth surface by a user is impossible according to this method.

DE 102006021640 B3 discloses a blank with a prefabricated, aesthetically relevant partial end surface of a tooth surface, wherein a planned 3-D model of the dental prosthesis is produced from this blank so that the prefabricated partial end surface of the blank remains unprocessed, at least in a central region, so that the prefabricated dental prosthesis already has a prefabricated partial surface.

A disadvantage of this method is that a large number of blanks with different prefabricated partial end surfaces must be provided in order to allow differently-shaped end dental prostheses to be produced in a dental laboratory or in the dental practice.

The object of the present invention is therefore to provide a method for producing a dental prosthesis that enables time-saving, simple and error-free production of dental prostheses having aesthetic surface structures.

DESCRIPTION OF THE INVENTION

The invention relates to a method for the virtual post-processing of a first virtual three-dimensional dental model of a dental prosthesis, said model having been created during the planning of the prosthesis. The first virtual truth model is virtually processed after planning in an additional method step by adapting at least one three-dimensional aesthetic surface structure already in existence to the first dental model by means of a virtual tool with the aid of a computer and a display device, and by subsequently inserting said structure into the first dental model The aesthetic surface structure has a predetermined shape, size and/or a predetermined insertion depth. After the adaptation, a tooth surface of the dental model is at least partially replaced with the adapted aesthetic surface structure. The aesthetic surface structure to be adapted is virtually processed in that a specific, selected parameter of the aesthetic surface structure is varied between a first value and a second value of the selected parameter by adjusting the virtual tool between a first end position and second end position, wherein the parameter of the aesthetic surface structure is a position of the surface structure relative to the planned first dental model, an orientation of the aesthetic surface structure relative to the first dental model, the shape and the size of the aesthetic surface structure, and/or an impression depth of the aesthetic surface structure relative to an original smooth surface of the original first dental model.

The present method is carried out only after planning a dental prosthesis in a post-processing step, wherein the aesthetic surface structures are inserted.

The dental prosthesis to be planned can be a part of a tooth such as a partial crown, an onlay, an inlay or a veneer, or an entire tooth such as a full crown, or a plurality of teeth of a dental arch connected with each other or arranged separate from each other. The first dental model can be a part of the dental prosthesis or the entire prosthesis. To post-process the first digital model, it can be visually separated from the remaining model of the dental prosthesis, or from a three-dimensional image of the surrounding tooth structure such as the neighboring teeth or a remaining tooth, by visually hiding the surrounding tooth structures of the image.

The virtual tool is used manually by means of a computer and the input means connected thereto such as a mouse or a keyboard, wherein the first dental model and the aesthetic surface structure to be adapted are visually depicted by means of the display device such as a monitor. The selected aesthetic surface structure is hence adapted to the dimensions of the first dental model and then inserted into said model so that the result of the method is a dental model with aesthetic surface structures.

The use of virtual tool hence yields an adaptation of the aesthetic surface structure which can be accomplished by means of specific algorithms, wherein the angular relationships and length relationships to the surrounding surface points remain the same when a surface structure of the virtual dental model is changed. The shape and dimension of the surface structure are therefore also retained in an enlargement or a reduction. The adaptation can also be performed iteratively in small steps over the entire time of using the virtual tool so that, when the surface structure is inserted into the first dental model, a smooth transition to neighboring surface points of the data model is ensured.

The virtual tool can, for example, be a virtual slide control or a virtual rotary control which enables a specific parameter, such as the impression depth, to be adjusted between two end positions.

The aesthetic surface structures can, for example, be fissures, characteristic recesses, horizontal individual patient growth grooves (so-called perikymata, imbrication lines or Retzius strips) which appear in the microsection of the tooth as concentric circles, or vertical grooves that, for example, consist of two so-called proximal marginal ridges of the tooth and a central ridge. In addition, characteristic surface structures can also have irregular, small notches and recesses with a patient-individualized distribution and shape. The aesthetic surface structures can also be shaped so that so they cause a natural play of light on the tooth surface by reflection and irregular light refraction and thereby imitate an aesthetic, visual impression of a natural tooth.

An advantage of this method is that the aesthetic surface structures are inserted during the virtual planning of the dental model so that the dental prosthesis is ground with a CAD/CAM machine tool from a blank that already has aesthetic surface structures in the visible ascetic surfaces, such as a labial surface of incisors and a buccal surface of buccal teeth. This eliminates the manual post-processing step in which the aesthetic surface structures must be manually introduced by a dental technician.

According to this method, the user therefore can, by means of the virtual tool, directly influence the surface structure to be inserted with regard to the selected parameters such as the impression depth. If the insertion depth changes, all of the recesses can be enlarged or reduced to the same extent in relation to the original smooth surface so that the user, such as a dentist or a dental technician, can evaluate whether a natural aesthetic impression is achieved with reference to a graphic representation of the first dental model having the surface structure to be varied.

Advantageously, the virtual tool is designed in the form of a slide control, wherein the aesthetic surface structure which is displayed by a display device is varied with reference to the selected parameter between a selected first basic surface structure with the first value of this parameter, and a selected second basic surface structure with the second value of this parameter by virtually shifting the slider between the first end position and the second end the position.

This allows the user to adapt the surface structure with regard to the selected parameter by using the slide control. The user can adapt the surface structure in regard to size in the first step, and in regard to the impression depth in the second step.

Advantageously, the aesthetic surface structure of a sample tooth can be selected from a database with sample teeth which are sorted according to size, age, dimensions and/or according to a tooth number or tooth type such as incisor, canine, pre-molar and molar.

This allows the user to correspondingly search for an appropriate sample tooth in the database depending on the size, the tooth type or tooth number according to the international FDI tooth chart. Then a partial surface of this sample tooth with aesthetic surface structures is automatically or manually selected, adapted to the first dental model and inserted.

Advantageously, the aesthetic surface structure to be adapted can be adopted from an average tooth, which is generated using a primary axis analysis method and an optimization method of the smallest square based on a plurality of natural teeth to be measured, and/or sample teeth by adapting to the dimensions and size of the first dental model.

A generic tooth model data set of a specific tooth type is thereby generated from a plurality of recorded tooth models, wherein factors of at least the primary components are varied, for example, linearly so that specified optimization criteria are satisfied by minimizing an error function, such as an error function of the least square and thereby adapt the selected aesthetic surface structure to the first tooth model. The primary components are determined in this case by the main axis analysis method.

Advantageously, the aesthetic surface structure to be adapted can be selected from a three-dimensional optical image of a residual tooth region, a neighboring tooth, a contralateral tooth and/or an opposing tooth with reference to the dental prosthesis, wherein the aesthetic surface structure to be adapted of a specific aesthetic surface such as a labial surface of incisors, and/or a buccal surface and an occlusal surface of buccal teeth is automatically selected by the computer using sample recognition algorithms, or manually by a user using the display device.

Consequently, a three-dimensional optical measurement of the dental situation is performed before planning, wherein in particular the remaining tooth region of a preparation for the dental prosthesis, the neighboring teeth, the contralateral tooth, and/or opposing tooth or opposing teeth is recorded. As a starting point for the present method, a partial surface with aesthetic surface structures of one of these teeth is selected and then adapted to the first data model and inserted. In particular, this allows the aesthetic impression of the contralateral tooth or neighboring to be imitated.

Advantageously, when planning the dental prosthesis part, at least one second dental model of a contralateral tooth can be planned in addition to the first dental model, wherein the surface structure to be adapted to the first dental model is inserted into the second dental model of the contralateral tooth using a mirroring algorithm, wherein the mirrored surface structure is only inserted into the second dental model after adapting the surface structure to the first dental model or simultaneous to adapting the surface of structure to the first dental model.

This enables the simultaneous insertion of an aesthetic surface structure in the contralateral tooth which reduces the time of planning.

Advantageously, the aesthetic surface structure to be adapted is controlled such that the adapted, generated aesthetic surface structure has an overcontouring with an impression depth relative to a smooth surface of the unprocessed first dental model that is greater than that of a natural tooth, so that material is removed from the produced dental prosthetic part in a polishing step of the dental prosthetic part after being generated with a CAD/CAM machine tool, and the generated aesthetic surface structure, in terms of the impression depth, corresponds to a surface structure a natural tooth from a three-dimensional optical image of a residual tooth region, a neighboring tooth, a contralateral tooth and/or an opposing tooth with reference to the dental prosthesis to be used.

The over-contouring of the aesthetic surface structure is thereby dimensioned so that the insertion depth of natural teeth is achieved after the polishing step.

Advantageously, the planned dental prosthesis with the adapted aesthetic surface structure can be created from a blank by means of a CAD/CAM machine tool.

The finished dental prosthesis with the aesthetic surface structure is thereby automatically created from the blank by means of the CAD/CAM machine tool.

BRIEF DESCRIPTION OF THE DRAWINGS

The invention is illustrated with the aid of the following drawings. In the drawings.

EXEMPLARY EMBODIMENTS

Figure 1:
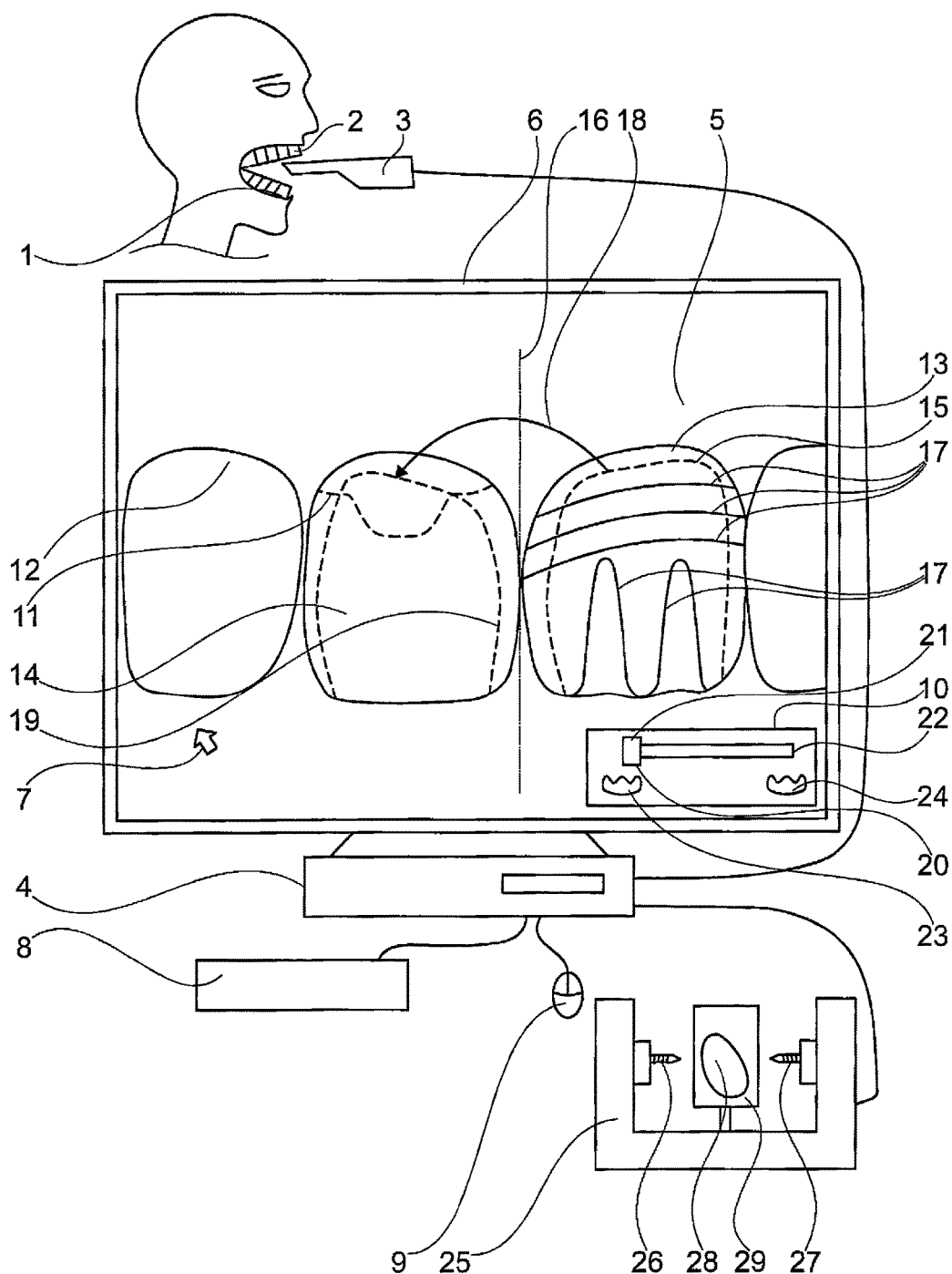
FIG. 1 shows a sketch to illustrate the present method.

FIG. 1 shows a sketch to illustrate the present method. In a first step, the dental situation comprising, for example, a mandible 1 or a maxilla 2, is recorded by means of an optical, three-dimensional digital camera 3, wherein the digital camera is based on a fringe projection method in the present case. The generated image data of the camera 3 are sent to a computer 4 that assembles the individual images into a three-dimensional visual image of the dental situation. The three-dimensional visual image 5 is displayed by means of a display device 6, such as a monitor. The user, such as a dentist or a dental technician, can navigate within the three-dimensional image 5 using a cursor 7 by means of the input device such as a keyboard 8 and a mouse 9 and operate a virtual tool 10 in the form of a slide control. Taking into account the dimensions of a remaining tooth 11, a first neighboring tooth 12 and a second neighboring tooth 13, and taking into account the opposing teeth (not shown), a first virtual three-dimensional dental model 14 of a digital prosthesis to be inserted—in the present case an individual tooth—is calculated using automated algorithms and/or manually adapted. After the first dental model 14 is planned, the present method begins, wherein a partial surface 15 of the neighboring tooth, which is simultaneously also a contralateral tooth with respect to a central axis 16, is selected in a post-processing step. The partial surface 15 is depicted in a dashed line and contains aesthetic surface structures 17, such as horizontal growth grooves and vertical grooves, which are sketched for the sake of illustration. Then the selected partial surface 15 with the aesthetic surface structures 17 is mirrored across the central axis 16 using a mirroring algorithm as indicated by the arrow 18. In the next step, the mirrored partial surface 15 with the aesthetic surface structures 17 is adapted to the first dental model 14 and is then inserted, wherein the original partial surface 19 with the smooth surface is replaced by the new adapted partial surface with the aesthetic surface structures. In this manner, aesthetic surface structures 17 are added to the first dental model 14. In the present case, the dental prosthesis to be inserted is an incisor so that the partial surface 15 to be inserted corresponds to the aesthetic surface structures 17 of a labial surface. In the case of a buccal tooth, the visible aesthetic surfaces, such as the buccal surface and/or the occlusal surface, are provided with aesthetic surface structures.

During adaptation, the partial surface 15 comprising the surface structures 17 is varied with reference to the specified parameters, such as the shape, size, and/or an insertion depth. In the present case, the first virtual tool 10 is used to vary the parameters of the insertion depth, wherein a slide bar 20 is moved between a first end position 21 and a second end position 22, wherein during the movement, the aesthetic surface structures 17 are changed with reference to the selected parameter of the insertion depth between a first basic surface structure 23 with a high insertion depth and a second basic surface structure 24 with a lower insertion depth. The slide bar 20 is accordingly a mixing controller such that the intermediate positions between the two end positions 21 and 22 represent combinations of the two basic surface structures 23 and 24. This allows the user to easily select the insertion depth. According to the present method, an individual basic surface structure can also be selected, and only the weighting of this basic surface structure can be changed by the slide control proceeding from the smooth partial surface 19. Then in the last step, the surface information of the first dental model 14 with the inserted surface structures 17 is translated into machine commands and sent to a conventional CAD/CAM machine tool 25, wherein the CAD/CAM machine tool 25 creates the dental prosthesis 28 to be produced from a blank 29 by means of the processing tools 26 and 27.

Figure 2:
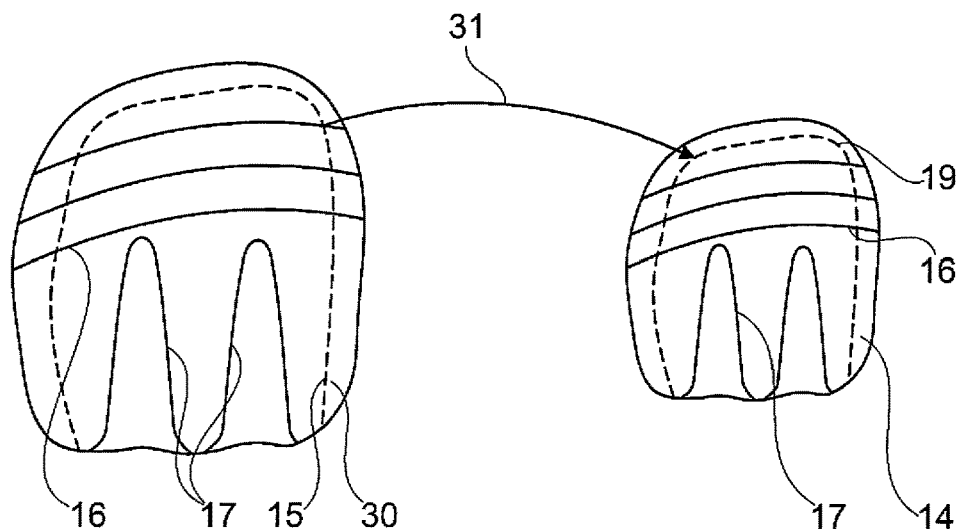
FIG. 2 shows usage of the virtual tool on a selected partial surface of a sample tooth.

FIG. 2 shows a use of a virtual tool 10 on the selected partial surface 15 of a sample tooth 30 from a database with sample teeth that are sorted according to size, dimensions and/or the tooth type. In the present case, the size of the sample tooth 30 is significantly greater than the dimensions of the first dental model 14 so that, by means of the virtual tool 10, the partial surface 15 with the aesthetic surface structures 17 can be reduced and added to the first dental model 14 as indicated by the arrow 31. The original partial surface 19 which is represented by a dashed line is thereby replaced with the reduced partial surface 15.

Figure 3:
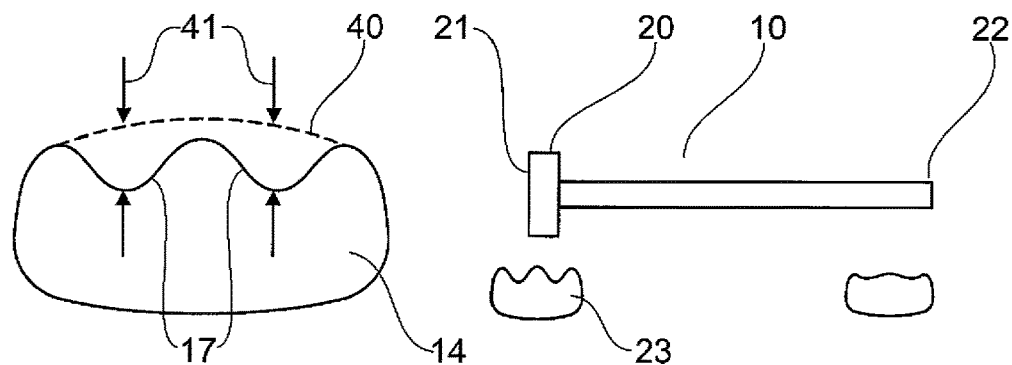
FIG. 3 shows a sketch to illustrate the adjustment of the impression depth in a first end position of the slide control.

FIG. 3 shows a sketch to illustrate the adjustment of the insertion depth by means of the virtual tool 10 from FIG. 1. The first dental model 14 is depicted in a cross-section from an incisal direction, wherein the vertical grooves 17 are clearly different from the original smooth surface 40 of the original tooth model 14 which is shown in a dashed line. The sliding bar 20 is moved to the first end position 21 so that the first basic surface structure 23 is set, and an insertion depth 41 has the highest value.

Figure 4:
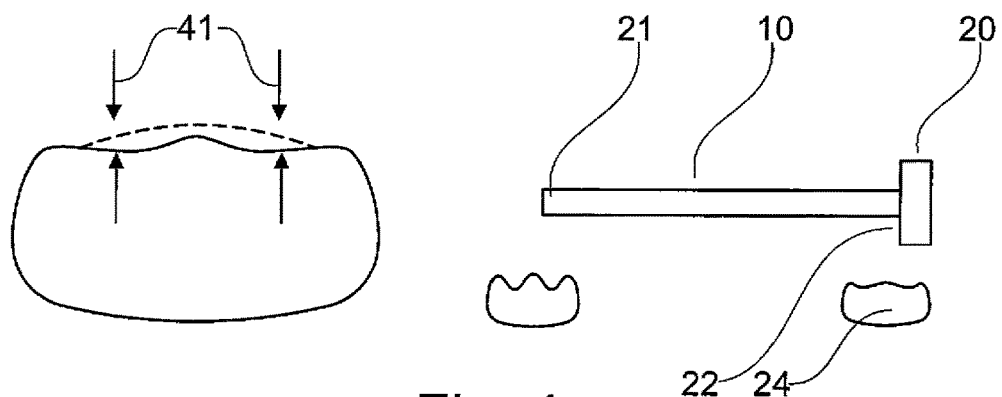
FIG. 4 shows a sketch to illustrate the adjustment of the impression depth in a second end position of the slide control.

In FIG. 4, the slide bar 20 is shown in the second end position 22, wherein the second basic surface structure 24 is set, and the insertion depth 41 is set at a minimum. When the slide bar 20 moves between the two end positions 21 and 22, the insertion depth 41 is accordingly changed and controlled. The insertion depth 41 can be changed in a linear manner.

REFERENCE CHARACTERS

1 Mandible
2 Maxilla
3 Three-dimensional dental camera
4 Computer
5 Three-dimensional optical image
6 Display device; monitor
7 Cursor
8 Keyboard
9 Mouse
10 Virtual tool; slide control
11 Remaining tooth
12 First neighboring tooth
13 Second neighboring tooth
14 First three-dimensional tooth model
15 Partial surface of the tooth model
16 Center axis
17 Aesthetic surface structures
18 Mirroring algorithm across the center axis
19 Original smooth partial surface
20 Sliding bar
21 First end position
22 Second end position
23 First basic surface structure
24 Second basic surface structure
25 CAD/CAM machine tool
26 Processing tool 27 Processing tool
28 Dental prosthesis to be produced
29 Blank
30 Sample tooth
31 Reduction of the surface structures
40 Original smooth surface of the tooth model
41 Insertion depth

The invention claimed is:

1. A method for the virtual post-processing of a first dental model of a dental prosthesis, said model being a virtual three-dimensional model and having been created during the planning of the prosthesis, the method comprising the steps of:
adapting, after the planning of the prosthesis, at least one three-dimensional aesthetic surface structure to the first dental model using a virtual tool with the aid of a computer and a display device by varying a specific, selected parameter of the at least one three-dimensional aesthetic surface structure between a first value and a second value through adjusting the virtual tool between a first end position and a second end position,
modifying the first dental model by inserting said adapted at least one three-dimensional aesthetic surface structure into the first dental model by partially replacing a tooth surface of the first dental model with the adapted at least one three-dimensional aesthetic surface structure, and
fabricating a dental prosthetic part based on the modified first dental model,
wherein the at least one three-dimensional aesthetic surface structure has a predetermined form, a predetermined size and/or a predetermined impression depth, and
wherein the specific, selected parameter is selected from the group consisting of a position of the at least one three-dimensional aesthetic surface structure relative to the planned first dental model, an orientation of the at least one three-dimensional aesthetic surface structure relative to the first dental model, a shape and size of the at least one three-dimensional aesthetic surface structure, and/or an impression depth of the at least one three-dimensional aesthetic surface structure relative to an original smooth surface of the first dental model.

2. The method according to claim 1, wherein the virtual tool is a slide control, and the specific selected parameter is varied between a selected first basic surface structure, and a selected second basic surface structure.

3. The method according to claim 1, wherein the at least one three-dimensional aesthetic surface structure of a sample tooth is selected from a database having sample teeth which are sorted according to size, age, dimensions, tooth number, and/or tooth type.

4. The method according to claim 1, wherein the at least one three-dimensional aesthetic surface structure to be adapted is adopted from an average tooth which is generated using a primary axis analysis method and an optimization method of the smallest square based on a plurality of natural teeth to be measured, and/or sample teeth.

5. The method according to claim 1, wherein the at least one three-dimensional aesthetic surface structure to be adapted is selected from a three-dimensional optical image of a residual tooth region, a neighboring tooth, a contralateral tooth and/or an opposing tooth with reference to the dental prosthesis.

6. The method according to claim 5, wherein the at least one three-dimensional aesthetic surface structure to be adapted is from a specific aesthetic surface such as a labial surface of incisors, and/or a buccal surface and an occlusal surface of buccal teeth.

7. The method according to claim 6 wherein the at least one three-dimensional aesthetic surface is selected automatically by the computer using sample recognition algorithms, or manually by a user using the display device.

8. The method according to claim 1, wherein when planning the dental prosthesis, at least one second dental model of a contralateral tooth is planned in addition to the first dental model,
wherein the at least one three-dimensional aesthetic surface structure to be adapted to the first dental model is inserted into the second dental model of the contralateral tooth using a mirroring algorithm after adapting the at least one three-dimensional aesthetic surface structure to the first dental model, or simultaneously to adapting the at least one three-dimensional aesthetic surface structure to the first dental model.

9. The method according to claim 1, further comprising controlling the at least one three-dimensional aesthetic surface structure to be adapted such that it has an overcontouring with an impression depth relative to a smooth surface of the first dental model that is greater than that of a natural tooth, so that material is removed from the fabricated dental prosthetic part in a polishing step of the dental prosthetic part after being generated with a CAD/CAM machine tool.

10. The method according to claim 9, wherein the at least one three-dimensional aesthetic surface structure generated on the fabricated dental prosthetic part, corresponds in terms of the impression depth, to a surface structure of a natural tooth from a three-dimensional optical image of a residual tooth region, a neighboring tooth, a contralateral tooth and/or an opposing tooth with reference to said dental prosthesis.

11. The method according to claim 1, characterized in that the planned dental prosthetic part is created from a blank with the adapted aesthetic surface structure by means of a CAD/CAM machine tool.

12. The method according to claim 1, further comprising selecting a partial surface of a sample tooth, said partial surface including the at least one three-dimensional aesthetic surface,
mirroring said partial surface across a central axis using a mirroring algorithm,
adapting the mirrored partial surface to the first dental model, and
inserting said adapted mirrored partial surface into the first dental model, wherein an original partial surface of the first dental model is replaced by the adapted mirrored partial surface having the at least one three-dimensional aesthetic surface structures.

13. The method according to claim 12, wherein the sample tooth is selected from the group consisting of a natural tooth from a three-dimensional optical image of a residual tooth region, a neighboring tooth, a contralateral tooth and/or an opposing tooth with reference to said dental prosthesis.

* * * * *